United States Patent [19]
Butz

[11] Patent Number: 6,017,721
[45] Date of Patent: Jan. 25, 2000

[54] CHROMATOGRAPHIC METHOD AND DEVICE FOR PREPARING BLOOD SERUM FOR COMPATIBILITY TESTING

[75] Inventor: Robert Butz, Odenton, Md.

[73] Assignee: The United States of America as represented by the Department of Health and Human Services, Washington, D.C.

[21] Appl. No.: 08/789,096

[22] Filed: Oct. 11, 1996

Related U.S. Application Data

[60] Provisional application No. 60/005,548, Oct. 18, 1995.

[51] Int. Cl.[7] ...................... G01N 33/543; G01N 33/548; G01N 33/564; G01N 33/80
[52] U.S. Cl. .......................... 435/7.25; 422/68.1; 422/72; 436/506; 436/518; 436/528; 436/529; 436/13; 436/825; 530/413; 530/868; 435/287.1; 435/288.6; 435/962; 435/975
[58] Field of Search ............................... 435/7.25, 287.1, 435/288.6, 962, 975; 530/413, 389.6, 868; 436/506, 518, 524, 528, 529, 13, 71, 807, 825; 422/68.1, 72

[56] References Cited

U.S. PATENT DOCUMENTS

| | | | |
|---|---|---|---|
| 4,666,831 | 5/1987 | Janoff et al. | 435/13 |
| 4,950,712 | 8/1990 | Letouneur et al. | 525/54.2 |
| 5,258,503 | 11/1993 | Yokohari et al. | 530/415 |
| 5,344,758 | 9/1994 | Krilis et al. | 436/518 |

OTHER PUBLICATIONS

McNeil et al., 1991. Immunology and Clinical Importance of Antiphospholipid Antibodies. Adv. Immunol. 49: 193–280.
Sigma Chemical Company Catalog, 1992. p. 1589.
Miller et al., 1996. Rapid adsorption of warm autoantibodies using polyethylene glycol. Transfusion 36: 20S, Abstract #S78.
Ylagan et al., 1996. Differential adsorptions using polyethylene glycol (PeG). Transfusion 36: 20S, Abstract #S79.
American Association of Blood Banks, *Technical Manual*, "The Antiglobulin Test," Chapter 8, 11th Edition (1993).
American Association of Blood Banks, *Technical Manual*, Identification of Unexpected Alloantibodies, Chapter 15, 11th Edition (1993).

Antonio Tobia Colucci, et al., "Blood Antiphospholipid Antibody Levels Are Influenced by Age, Sex and HLA–B8, DR3 Phenotype," *Exp Clin Immunogenet* 9:72–79 (1992).
Del Papa, N., et al., "Antiphospholipid Antibodies Cross–Reacting with Erythrocyte Membranes. A Case Report," *Clinical and Experimental Rheumatology* 10:395–399 (1992).
Harris, E.N., et al., "Antiphospholipid Antibodies: Method of Detection," *American Journal of Reproductive Immunology* 28:208–210 (1992 Munksgaard).
Levy, Roger A., et al., "Fatty Acid Chain is a Critical Epitope for Antiphospholipid Antibody," *Journal of Clinical Immunology*, vol. 10, No. 3 (1990).
Qamar, Tasneem, et al., "Lysophosphatidylethanolamine Is the Antigen to Which Apparent Antibody to Phosphatidylethanolamine Binds," *Journal of Clinical Immunology*, vol. 10, No. 4 (1990).
Sammaritano, Lisa R., et al., "Antiphospholipid Antibody Syndrome: Immunologic and Clinical Aspects," *Seminars in Arthritis and Rheumatism*, vol. 20, No. 2, pp. 81–85 (Oct., 1990).
Talen, Marilyn J., "Erythrocyte Blood Group Antigens: Not So Simple After All", *The Journal of The American Society of Hematology*, Blood, vol. 85, No. 2, pp. 299–306 (Jan. 15, 1995).
Triplett, Douglas A., "Antiphospholipid Antibodies: Proposed Mechanisms of Action", *American Journal of Reproductive Immunology*, 28:211–215 (1992 Munksgaard).

*Primary Examiner*—Christopher L. Chin
*Assistant Examiner*—James L. Grun
*Attorney, Agent, or Firm*—Townsend and Townsend and Crew LLP

[57] ABSTRACT

The invention provides a new method for antiglobulin testing from serum of a potential blood transfusion recipient in which warm autoantibodies are removed from serum so as to allow identification of alloantibodies present. The method involves contacting serum from a patient with one or more ligands that bind warm autoantibodies but do not bind alloantibodies, separating the non-bound serum components from the bound warm autoantibodies, and using the warm autoantibody-depleted serum in antiglobulin testing. Suitable ligands include phospholipids, the polar head groups of phosphoglycerides, and naturally occurring and synthetic analogues of these molecules.

20 Claims, 5 Drawing Sheets

CHROMATOGRAPHIC METHOD AND DEVICE FOR PREPARING BLOOD SERUM FOR COMPATIBILITY TESTING

This application claims the benefit of U.S. Provisional Application Ser. No.60/005,548, filed Oct. 18, 1995.

FIELD OF THE INVENTION

This invention provides for devices and methods for chromatographically treating blood for use in compatibility assays. These assays are used to ensure that donor blood is safe. The devices comprise phospholipid-like compounds bound to solid supports that are used to cleanse the blood samples.

BACKGROUND OF THE INVENTION

Blood transfusion is a common medical procedure that may be indicated for treatment of hemorrhage, hypoplastic anemia, hemolytic anemia, and other conditions. Although blood transfusion is a life-saving procedure, it carries with it the danger of an immune-mediated reaction by the transfusion recipient against the foreign (donor) cells. For example, if red blood cells (RBCs) are transfused into a recipient who mounts an immune response against the cells, an immune transfusion reaction may occur. The symptoms of a transfusion reaction can include malaise, fever, shock and renal failure, and will depend, in part, on whether whole blood or a blood component is transfused and on the particular antigen to which the immune response is mounted.

Because of the possibility of a transfusion reaction, it is routine for bloodbank practitioners to take steps to ensure that transfusion of the donor cells into a recipient results in a minimal immune response. This is done by determining the ABO and Rh types of a prospective transfusion recipient, and testing the recipient's serum for compatibility with the donor's red blood cells (e.g, by cross-matching or compatibility testing) prior to transfusion. In blood banking practice this screening usually begins with a triad of routine tests: an ABO test, a direct antiglobulin (Coombs) test, and an "antibody screening test." The ABO test is used to determine blood type. The direct Coombs test uses anti-IgG to agglutinate a patient's RBCs and, if positive, indicates that IgG are present on the surface of the patient's RBCs and suggests that an autoimmune response has been raised against these cells. The antibody screening test is used to detect the presence of an unexpected antibody in a patient's serum using reagent RBCs of known phenotype. If the antibody screen indicates that an alloantibody is present in the sample, another test such as a "compatibility test" (also known as a "panel test") is carried out to identify the classes of clinically significant alloantibodies, if any, in the recipient's serum. Panel tests consist of a series of Group O reagent RBC samples with known blood group phenotypes. The recipient's serum is combined with reagent RBCs of each phenotype, and the pattern of binding allows determination of what alloantibodies are present in the recipient's serum. For example, serum containing anti-$Fy^a$ alloantibodies will react with RBCs expressing the $Fy^a$ (Duffy) antigen but would not necessarily bind RBCs displaying other antigens. The term "antiglobulin test" is used to describe tests that can be used to identify alloantibodies. Antiglobulin tests are described in the *American Association of Blood Banks (AABB) Technical Manual* 11th Edition (1993) Bethesda, Md., which is incorporated herein by reference, at, e.g., pages 175–187. Indirect antiglobulin tests include antibody detection, antibody identification, and compatibility testing. When an indirect antiglobulin test is performed on a donor unit in preparation for infusion, it is referred to as compatibility testing. When the test is done on reagent red cells it is referred to as antibody identification or antibody screening.

Identification of alloantibodies in the recipient's serum by cross-matching or panel testing is important because some alloantibodies will react with, and rapidly destroy, transfused cells displaying the corresponding antigen. This results in a hemolytic transfusion reaction with potentially serious consequences for the recipient. Thus, whenever possible, patients with clinically significant alloantibodies should receive blood that has been found to lack the corresponding antigen. Alloantibodies are sometimes referred to as "unexpected alloantibodies" to distinguish them from anti-A or anti-B antibodies.

In some cases the antibody screen and/or panel test indicate that the recipient's serum contains antibodies that react with RBCs generally. When this result is accompanied by a positive Coombs test, a conclusion is made that the recipient's serum contains antibodies, referred to as warm autoantibodies, that react with antigens present on all RBCs. The name "warm autoantibodies" refers to the fact that these antibodies react optimally with RBCs at 37° C. (in contrast to the cold agglutinins, which attach to red cells only when the temperature is below 37° C. and dissociate from the cells when the temperature rises above 37° C.) It has generally been believed that warm autoantibodies are primarily specific for Rh antigen and other protein antigens on RBCs. Warm autoantibodies are associated with conditions such as "warm antibody autoimmune hemolytic anemia;" however, not all patients with warm autoantibodies in their serum exhibit signs of anemia.

Because warm autoantibodies bind RBCs indiscriminately they mask the binding by alloantibodies to certain classes of RBCs in a panel test, making it impossible to determine what alloantibodies are present in a serum sample. For this reason, in order to detect alloantibodies it is necessary to first remove warm autoantibodies from a sample of the recipient's serum. According to current blood banking practice, warm autoantibodies are removed from a sample by a process such as autologous adsorption. In this procedure, red blood cells are obtained from the recipient and treated (for example, using chloroquine diphosphate or DTT with cysteine-activated papain) in order to elute autoantibody bound to them. The treated cells are then used to adsorb patient sera to remove warm autoantibody (e.g., by combining the enzyme-treated RBCs with an equal volume of serum, incubating for 60 minutes at 37° C., and separating the cells from the adsorbed serum by centrifugation). The adsorbed serum is then used in a panel test against antibody screening cells. If all the cells in the panel remain positive, the autoadsorption procedure is repeated. It typically takes about 1.5 hours to complete one round of cell preparation and adsorption, and three to four rounds of absorption may be required to ensure removal of a sufficient amount of the warm autoantibody. Thus, it typically takes 4–6 hours to remove warm autoantibody from a serum sample. An alternative adsorption protocol in which allogenic RBCs are used for adsorption is employed when the patient has been recently transfused or when insufficient rbcs are available for autoadsorption.

The techniques available for removing warm autoantibodies from serum are time-consuming, tedious, and may require large amounts of cells and sera. Faster and more convenient methods are desirable and would be of great benefit to patients and health workers. In accordance with this need, the present invention provides new methods for antiglobulin testing that use methods other than autoadsorption for removing warm autoantibodies from serum.

SUMMARY OF THE INVENTION

The present invention provides a new method for antiglobulin testing from serum of a potential blood transfusion recipient. Specifically the invention provides a new way of removing warm autoantibodies from serum so as to allow identification of alloantibodies present. The method includes the following steps: (a) obtaining a test sample of serum or plasma from a patient, (b) contacting the test sample with one or more ligands synthetically conjugated to an immobilized support, where the ligands bind warm autoantibodies but not alloantibodies, with the further proviso that the ligands do not bind anti-RH antibodies, (c) separating the non-bound serum components including alloantibodies (if present) from the bound warm autoantibodies, and (d) using the non-bound serum components (i.e., warm autoantibody-depleted serum) in antiglobulin testing.

A variety of warm autoantibody-binding ligands are suitable for use in the invention, including phospholipids (i.e., phosphoglycerides), phosphoric acid esters typically associated with phospholipids, but free of the fatty acid moiety or free of both the fatty acid and glycerol moieties characteristic of phospholipids (e.g., the polar head groups of phosphoglycerides; see, e.g., Lehninger, A. L. *Biochemistry*, 2d Edition, 1975, Worth Publishers, New York, which is incorporated herein by reference), and naturally occurring and synthetic analogues of the above-recited molecules. Compounds such as O-phospho-DL-serine, O-phospho-L-serine, O-phospho-L-threonine, 3-phosphoglyceric acid, phosphatidylcholine, and phosphocholine, used individually or in combination, are especially preferred as ligands.

The invention also provides a kit containing a column, such as a spin column, one or more warm autoantibody-binding ligands, such as 3-phosphoglyceric acid and phosphocholine, and instructions for removing warm autoantibodies from a test sample for use in antiglobulin testing.

A method for neutralizing warm autoantibodies without removing them from the serum is also provided. According to this method, a warm autoantibody binding ligand, such as a phospholipid, is added to a serum sample in an amount sufficient to neutralize any warm autoantibodies present. The serum is then used for antiglobulin testing.

DETAILED DESCRIPTION

I. Introduction

The present invention is a new method for antiglobulin testing from serum of a potential blood transfusion recipient. The method includes the step of removing warm autoantibodies from a test sample of the recipient's serum by contacting the serum with an immobilized ligand to which warm autoantibodies bind. The new method will be used advantageously when the recipient's serum contains antibodies that interfere with the identification of alloantibodies in the recipient's serum. This new method has several advantages over the existing method of autologous autoadsorption. The new method is less time consuming than existing methods and will shorten the delay in, e.g., compatibility testing and subsequent transfusion support in patients. In addition the new method is expected to be less expensive than methods now used. Finally, the new method will require less serum from the patient and require handling of less serum by medical workers.

The invention is based in part on the discovery that among patients expressing warm autoantibodies, many express antibodies that specifically bind to a phosphoric acid ester such as those associated with naturally occurring phospholipids. Surprisingly, the fatty acid moiety of a phospholipid is not required for binding. Based on this discovery it is surprisingly possible to remove warm autoantibodies from many or most serum samples in which they are present by incubating warm autoantibody-containing serum and an immobilized ligand of the sort described. Surprisingly, sufficient warm autoantibody may be removed from many or most serum samples using a single round of chromatography to allow identification of clinically significant alloantibodies to be rapidly carried out.

II. Warm autoantibodies

The present method will be useful any time that removal of warm autoantibodies from a test sample for antiglobulin testing is desired. The term warm autoantibodies, as generally used in the blood-banking art and as used herein, refers to antibodies directed against RBCs that interfere with alloantibody testing. For example, a serum sample that tests positive for all RBCs in an antiglobulin test will be believed to contain warm autoantibodies if the serum comes from a patient whose RBCs also test positive in a Coombs test. Thus, as used herein, a recipient's serum sample is said to contain warm autoantibodies if (a) the recipient's RBCs test positive in a direct Coombs test or the equivalent and (b) the recipient's serum contains antibodies that bind all or virtually all reagent RBCs in a standard panel test such as the Ortho Diagnostic Systems Inc. Resolve™ Panel B or an equivalent similar test. Similar panel tests and methods for compatibility testing are described in *Issit, Applied Blood Group Serology* 2nd Edition 1992, Cooper Biomedical, One Technology Court, Malvern, Pa., which is incorporated by reference herein. Coombs tests are well known in the blood-banking art and are described in *Immunohematology-Zmijewski* 3rd Edition, e.g. at pages 42–44 and 307–308 and in Boorman, Dodd and Lincoln, *Blood Group Serology* 5th Edition 1992, e.g., at pages 60–65, 367–370, and 469–473 which are likewise incorporated by reference herein.

One of skill will recognize that although it may be desirable, it is not absolutely necessary to carry out a panel and a direct Coombs test before removing warm autoantibodies from the recipient's serum according to the present invention. Alternative serological tests, indications, or clinical observation (e.g., symptoms of immune hemolytic anemia or a diagnosis of systemic lupus erythematosus) that suggest the presence or likelihood of warm autoantibodies may be sufficient to warrant use of the invention. In some cases it may be desirable to use the invention routinely in the absence of serological or medical indications.

III. The recipient and donor

As used herein, the terms "recipient" and "patient" refer to the person who receives or is contemplated to receive a transfusion of a blood product (including whole blood, packed RBCs, platelets, or any other blood product that contains a sufficient amount of red blood cells, intentionally or as a contaminant, to elicit an immune response in the recipient). The term "donor" refers, according to context, to the cells to be transfused into the recipient or to the person in whom those cells originate.

IV. The serum test sample

A test sample comprises serum or plasma, most often serum. Plasma is the acelluler fraction of blood which contains water, proteins (including antibodies), inorganic salts, and other components. Serum is a fraction of blood plasma from which the clotting factor fibrinogen has been removed. Except where otherwise indicated, as used herein the term "serum" refers to both serum and plasma.

V. Alloantibodies and Other Serum Components

Alloantibodies are antibodies directed against RBCs. Alloantibodies do not react with antigens present on the RBCs of the antibody producer, but may react with donor RBCs. Immunization to foreign RBC antigens may result from pregnancy, transfusion, injection with immunogenic material, or through an unknown immunizing event. As used herein the term "alloantibodies" means clinically significant alloantibodies other than naturally occurring anti-A or -B. "Clinically significant alloantibodies" refers to antibodies that shorten the anticipated survival of transfused RBCs or has been associated with hemolytic disease of the newborn, although the degree of clinical significance varies. Examples of clinically significant alloantibodies are antibodies directed against RBC antigens listed in Table I.

TABLE I

| Blood Group System | antigen |
|---|---|
| Rhesus (Rh) | D |
|  | C |
|  | E |
|  | c |
|  | e |
|  | f |
|  | V |
|  | VS |
|  | $C^w$ |
| MNSs | M |
|  | N |
|  | S |
|  | s |
| P | $P_1$ |
| Lewis | $Le^a$ |
|  | $Le^b$ |
| Lutheran | $Lu^a$ |
|  | $Lu^b$ |
| Kell | K |
|  | k |
|  | $Kp^a$ |
|  | $Js^a$ |
| Duffy | $Fy^a$ |
|  | $Fy^b$ |
| Kidd | $Jk^a$ |
|  | $Jk^b$ |
| Sex-linked | $Xg^a$ |

For ease of reference it will be convenient in some cases to refer to serum as containing warm autoantibodies and "other serum components." The term "other serum components" is used in its ordinary sense to refer to any serum components other than warm autoantibodies (i.e., water, antibodies, other proteins, salts, etc.). Another term for "other serum components" is warm autoantibody-depleted serum.

VI. Conditions and methods for contacting the test sample and the ligand.

According to the invention a sample of a patient's serum is contacted with a ligand that binds warm autoantibodies but does not bind alloantibodies. The amount of serum used can vary, but will usually be between about 0.5 milliliters (mls) and 5 mls, most often 1 ml to 2 mls.

Conditions of pH, temperature, ionic strength and time are chosen so as to ensure binding of the warm autoantibodies to the ligand. In the most preferred embodiment the test sample is serum (as opposed to plasma) and is incubated neat (i.e., undiluted, except by addition of small amounts of anticoagulant agents) with the immobilized ligand at about 37° C. for between about 0.25 hours and 15 hours, usually about 0.5 hours. These conditions are chosen for ease and speed, however, one of ordinary skill will recognize that they may be varied. For example, it may sometimes be useful to incubate the ligand and serum at room temperature (e.g., about 25° C.) or at an even lower temperature (e.g., about 4° C.). Usually the incubation temperature will be between about 4 and 37° C. Similarly, although serum is often used without modification, it may sometimes be desirable to adjust the pH or ionic strength of the test sample. Typically the ionic strength will range from about 0.1 Normal (N) NaCl to about 1.5 N NaCl, often about 0.9 N. Usually the pH will be between about 5.5 and about 8, with about 7.0 preferred. In addition, additives such as "LISS" (Low ionic strength solution), PEG, albumin or polybrene may be added to increase alloantibody reactivity. See *Applied Blood Group Serology, supra*. Because of the need to carry out compatibility testing or cross-matching promptly, the time of incubation will usually be chosen to be the shortest time that will allow efficient removal of warm autoantibodies. However, it will be possible to extend the incubation time if desired. It will sometimes be desirable, especially when extended incubation times are used, to include protease inhibitors to prevent degradation of alloantibodies during the incubation. Useful protease inhibitors include PMSF, aprotinin, leupeptin and others.

In a preferred embodiment the test sample and ligand are incubated together in a chamber of a spin column such that handling of the blood product-containing sample by medical workers is minimized.

VII. Methods for separating immobilized ligand to which warm autoantibodies are bound from the unbound serum components.

Numerous methods for separating a bound antibody from unbound components (e.g., the unbound alloantibodies) are available and well known to those of skill. Common methods include chromatographic columns (e.g., affinity columns), filtration, magnetic separation, precipitation by centrifugation, immune precipitation, and others. The precise method of separating the immobilized ligand with bound warm autoantibodies from the other serum components (e.g., including alloantibodies, if present) is not critical but should be convenient and minimize handling and exposure of medical workers to blood products. In a preferred embodiment, bound warm autoantibody and unbound serum components are separated using column chromatography. In a particularly preferred embodiment a spin column is used.

VIII. The Ligand

One of the discoveries of the present invention is the determination that warm autoantibodies can be removed from a significant proportion of serum samples by contacting the serum with a ligand conjugated to a solid support, where the ligand is a phospholipid (i.e., a phosphoglyceride or a lysophosphoglyceride), a phosphoric acid ester typically associated with phospholipids, but free of the fatty acid moiety or free of both the fatty acid and glycerol moieties characteristic of phospholipids (e.g., the polar head groups of phosphoglycerides), or naturally occurring and synthetic analogues of the above-recited molecules. Prior to this discovery it was believed in the blood banking art that warm autoantibodies recognized primarily epitopes on proteins and glycoproteins found on RBCs. Although some warm autoantibodies are directed against protein antigens, it has now been discovered that many or most are directed against phospholipids. Moreover, in contrast to antiphospholipid antibodies previously described, it has been discovered that most warm autoantibodies do not require the fatty acid moiety of phospholipids for binding.

In its broadest sense the present invention is the use of a ligand that binds antiphospholipid antibodies to remove warm autoantibodies from serum for antiglobulin testing. The ligand can be any organic molecule that has a molecular weight of less than about 500 and contains phosphoric acid ester and which specifically binds warm autoantibodies. Thus, as used herein the terms "warm autoantibody-binding ligand" or "ligand" specifically exclude cell membranes (such as red blood cell ghosts), proteins (such as anti-warm autoantibody IgGs) or the like, even though warm autoantibodies might bind such macromolecules or membranes.

In one group of embodiments the ligand is a phospholipid such as phosphatidylethanolamine, phosphatidylcholine, phosphatidylserine, 3'-O-lysylphosphotidylglycerol, phosphatidylinositol, phosphatidylglycerol, or cardiolipin.

In a second group of embodiments, the ligand may be a phosphoric acid ester typically associated with phospholipids (i.e., a polar head group) such as phosphoethanolamine, phosphocholine, phosphoserine, phosphoinositol, phosphoglycerol, 3'-O-lysylphosphoglycerol and the diphosphoglycerol which is found in cardiolipin.

In a third group of embodiments the ligand may be naturally occurring or prepared from naturally occurring components of the above recited molecules. Examples include 3-phosphoglyceric acid, O-phospho-L-serine, O-phospho-DL-serine, O-phospho-L-threonine, O-phospho-L-tyrosine, phosphoenolpyruvic acid, Nω-phospho-L-arginine, phosphocolamine, 6-phosphogluconic acid, D-2-phosphoglyceric acid, O-phospho-D-serine, O-phosphoethanolamine, and O-phospho-D-threonine, and salts thereof.

In a fourth group of embodiments the ligand may be a synthetic mimic or analogue of any of the above recited molecules, such as 2-(phosphonomethyl)acrylic acid or Tris (cyclohexylamine)salt. For example, one ligand is glycerol 3-phosphoric acid inositol ester, a phosphoric acid ester typically associated with phosphatidylinositol. One of skill in the art will understand that the inositol portion of this compound can be replaced with other mono-, di- and polysaccharrides having a molecular weight less than about 500. Examples of such sugars include, glucose, galactose, fucose, lactose, and the like. Similarly, analogs of the polar head group derived from phosphatidylserine can be prepared by replacing the serine portion with other hydroxyacids, including 3-hydroxypropionic acid, homoserine, D-serine, D- or L-threonine, 3-hydroxy-2-methylpropionic acid and N-methyl serine. Analogs of the polar head group derived from phosphatidylcholine (or phosphatidylethanolamine) can be prepared by replacing the choline (or ethanolamine) portion of the phosphoric ester with, for example, 3-ammoniumpropanol, 2-ammoniumpropanol, 2-(N,N,N-triethylammonium)ethanol, 2-(N,N-dimethylammonium) ethanol, and related lower alkyl ammonium-ethanol, -propanol and other amino or ammonium lower alkanol species. Analogs of phosphatidylglycerol include those which are prepared by replacing the glycerol moiety with other lower alkyl polyols. As used herein the term "lower alkyl polyols" refers to an alkyl radical having of from 2 to 8 carbon atoms which is substituted by at least two hydroxyl groups. The alkyl portion can be straight chain or branched. It will be apparent to one of skill in the art, that analogs of the polar head groups can include many structures which vary in branching, degree of unsaturation and degree of substitution. Thus, for example, the analogs will include compounds which (a) can be considered homologs of phospholipids or polar head groups, or (b) which are phosphoric acid esters comprising an alkyl or aryl ester portion substituted with polar functionality (—OH, —NH$_3$+, —NH$_2$, —CO$_2$H) which is typically of the type and degree found in the naturally occurring phospholipids.

One of skill will recognize that other modifications to naturally occurring phospholipids can be made. For example, the fatty acid components of naturally occurring phospholipids may be replaced with other moieties, for example fatty acids differing in saturation from naturally occurring fatty acids, or other structures which vary in branching, degree of unsaturation and degree of substitution.

Particularly preferred warm autoantibody-binding ligands include O-phospho-D-serine, O-phospho-L-serine, O-phospho-DL-serine, O-phospho-L-threonine, O-phospho-D-threonine, 3-phosphoglyceric acid, O-phosphoethanolamine and phosphocholine.

The ligands described above will typically be attached to a solid support by a linking group to aid in the removal of warm autoantibodies from serum.

The proportion of warm autoantibody-containing serum samples from which warm autoantibodies can be removed using an immobilized ligand or combination of ligands will vary according to the ligand, but will usually be between about 20% and 95%, typically at least about 50% and often more than about 70%.

It will often be the case that a single ligand binds warm autoantibodies in test sera from a fraction (e.g., less than 90%) of patients with warm autoantibodies, but that a combination of two or more ligands will bind a higher fraction by acting in a complementary or additive fashion. Thus, in one embodiment the device includes at least two ligands. In a preferred embodiment the ligand is a combination of O-phospho-L-threonine and O-phospho-DL-serine. In a most preferred embodiment the ligand is a combination of phosphocholine and 3-phosphoglyceric acid.

Warm autoantibody binding ligands that are useful in the invention are those that do not bind clinically significant alloantibodies. Such cross-reactivity is unlikely because alloantibodies are directed against proteins rather than to phospholipids or polar head groups associated with phospholipids. However, this presumed absence of cross-reactivity can be easily verified using routine methods. For example, one method for determining whether a warm-antibody binding ligand binds alloantibodies is to incubate the ligand with serum samples containing known alloantibodies. The alloantibody content of a serum sample can be determined according to standard methods in a panel test. According to this assay, the serum is divided into two 1 ml. aliquots. One aliquot is incubated with the ligand to be tested (e.g., using 1 ml of activated agarose saturated with immobilized ligand, e.g., carrying about 1 gram of ligand, is sufficient) and then the immobilized ligand and any bound antibodies are separated from the other components. Both aliquots are then analyzed in a panel test. A suitable panel test would be one that tests for the antigens listed in Table I, for example the "Panel TWO and Ficin-Panel®TWO" test from Gamma®Biologicals, Inc. (Houston, Tex.).

Any significant reduction in alloreactivity would generally indicate that the ligand binds a clinically significant alloantibody and is not suitable for the invention.

IX. Immobilization of the warm autoantibody binding ligand

The ligand is synthetically conjugated via a linking group to an immobilized or immobilizable support matrix such as agarose, dextran, cellulose, polyacrylhydrazido-agarose, oxirane acrylic beads, derivatized paper, or polyacrylamide beads. These matrices are activated in a variety of ways known to those of skill in the art to allow easy conjugation of a warm autoantibody-binding ligand to the matrix. Examples of activated matrices and functional spacers can be found in the catalog of the Sigma Chemical Company, St. Louis, Mo. (1995), which is incorporated herein by reference, at, e.g., pages 1736–1739 and in the references cited therein. Examples of activated matrices include cyanogen bromide activated matrices, epoxy activated matrices, and nitrophenyl chloroformate and n-hydroxysuccinimide chloroformate activated matrices.

The linking group is preferably of sufficient length to permit the ligands to interact freely with the warm autoantibodies. The linking groups are typically 6–50 atoms long to provide sufficient exposure for the attached ligands and is comprised of a surface attaching portion and a longer chain portion. The surface attaching portion is that part of the linking group which is directly attached to the solid support. This portion can be attached to the solid support via carbon-carbon bonds using, for example, supports having (poly)trifluorochloroethylene surfaces, or preferably, by siloxane bonds (using, for example, glass or silicon oxide as the solid support). Siloxane bonds with the surface of the support are formed in one embodiment via reactions of surface attaching portions bearing trichlorosilyl or trialkoxysilyl groups. The surface attaching groups will also have a site for attachment of the longer chain portion. For example, groups which are suitable for attachment to a longer chain portion would include amines, hydroxyl, thiol, and carboxyl. Preferred surface attaching portions include aminoalkylsilanes and hydroxyalkylsilanes.

The longer chain portion which is to be used as part of the linking group can be selected based upon its hydrophilic/hydrophobic properties to improve presentation of the ligands to the warm autoantibodies. The longer chain portion can be constructed of polyethyleneglycols, polynucleotides, alkylene, polyalcohol, polyester, polyamine, polyphosphodiester and combinations thereof. More particularly, the linking group itself may be an alkylene group (of from about 6 to about 24 carbons in length), a polyethyleneglycol group (of from about 2 to about 24 ethyleneglycol monomers in a linear configuration), a polyalcohol group, a polyamine group (e.g., spermine, spermidine and polymeric derivatives thereof), a polyester group (e.g., poly(ethyl acrylate) having of from 3 to 15 ethyl acrylate monomers in a linear configuration), a polyphosphodiester group, or a polynucleotide (having from about 2 to about 12 nucleic acids). In one group of embodiments, the linking group is a polyethyleneglycol group which is at least a tetraethyleneglycol, more preferably, from about 1 to 4 hexaethyleneglycols linked in a linear array.

The ligand will be attached to the linking group by, for example, an ether, ester, carbamate or amine linkage. Methods of forming such linkages are known to those of skill in the art and particular reagents and references can be found in such texts as March, *Advanced Organic Chemistry*, 4th Ed., Wiley-Interscience, New York, N.Y., 1992, incorporated herein by reference.

The position of attachment of the ligand to the linking group can be at any of several locations on the ligand. For example, a ligand derived from phosphatidylethanolamine can be attached to a linking group (and solid support) through the ammonium groups of the ethanolamine position, or through any available hydroxy or amino group of the glycerol or substituted glycerol In a preferred embodiment, the column matrix is activated agarose beads such as adiptic acid dihydrazide-agarose (Sigma Chemical Co. Cat. # A 0802).

X. Spin column and Kit

Figure 1:
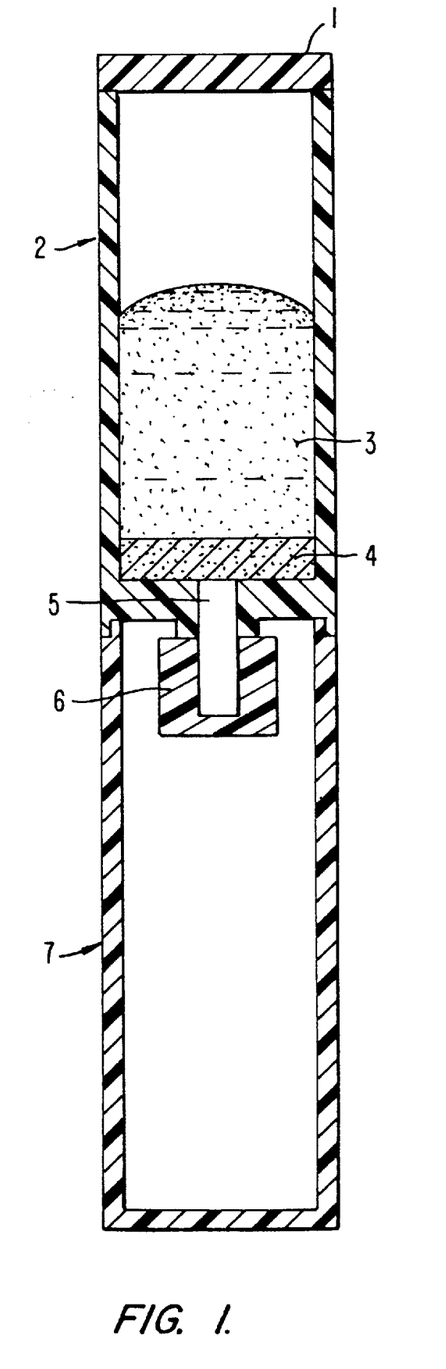
FIG. 1 provides a side view of a device of this invention illustrating a preferred means for treating sera by contacting the sera with the phospholipid-type ligands bound to a solid support.

When chromatography is used for separating the bound warm autoantibodies from the other serum components, a number of column designs and configurations may be suitable. In a preferred embodiment (FIG. 1) a "spin column" is used. Spin columns are well known in the art and are generally small (e.g., usually containing <5 milliliters of resin) and are adapted for low-speed centrifugation to rapidly remove bound materials from eluant. In one preferred embodiment the spin column will include an opening (1), with an optimal resealable cap, said opening leading to an upper chamber (2) containing the immobilized ligand(s) (3). Below the ligand bound matrix is a porous support (4) such as filter paper and below the support is an outlet (5) which is optionally sealable with a cap or plug (6). The outlet (6) leads to a lower chamber. The upper chamber (2) can be entirely or partially housed within the lower chamber. According to this embodiment the lower chamber is removable and both the upper and lower chambers can be reversibly sealed at both the top and the bottom. In a preferred embodiment the test sample is added to the upper chamber (which is sealed at the bottom to prevent leakage of the serum) and incubation takes place in the column. Following incubation the seal at the bottom of the spin column is broken or removed and the column centrifuged so as to allow the eluant to migrate out of the upper chamber and into a lower collecting chamber. The eluate (i.e., the warm autoantibody depleted serum or "other serum components") is then collected and used for antiglobulin testing.

In a preferred embodiment the upper chamber contains O-phospho-DL-serine and O-phospho-L-threonine, each conjugated to a support. In a most preferred embodiment the upper chamber contains 3-phosphoglyceric acid and phosphocholine, each conjugated to a support. The ratio of O-phospho-DL-serine to O-phospho-L-threonine, or of 3-phosphoglyceric acid to phosphocholine, when expressed as a molar ratio is usually between 1:10 and 10:1, preferably between 1:5 and 5:1 and most preferably about 1:1. In a preferred embodiment the support is activated agarose such as adiptic acid dihydrazide-agarose.

A kit useful for practicing the claimed invention is also contemplated. In one embodiment the kit will include a spin column. A spin column typically has a lower chamber and a removably housed upper chamber. In a preferred embodiment the upper chamber can be reversibly sealed at both the top and the bottom so that incubation of serum with ligand can be safely carried out in the upper chamber. The column will contain or be accompanied by immobilized warm autoantibody-binding ligands. In a preferred embodiment the ligands are O-phospho-D-serine and O-phospho-D-threonine, each conjugated to a support matrix. In a most preferred embodiment the ligands are phosphocholine and 3-PGA, each conjugated to a support matrix. The immobilized warm autoantibody-binding ligands may be provided in dry form or kept moist, e.g., with water or buffer. A suitable preservative such as sodium azide may also be included. The kit will also include instructions for preparing serum for antiglobulin testing using the spin column.

XI. Treatment of the test sample with a warm autoantibody-binding ligand

In an alternative embodiment, a suitable ligand is added to a test sample of serum in an amount sufficient to neutralize the warm autoantibodies present in the test sample (i.e., to saturate the binding sites of the antibodies). It will usually be sufficient to add 1 ml of a saturated suspension of the ligand per 10 mls of serum. The test sample is then used for antiglobulin testing.

EXAMPLES

The invention is illustrated by the following examples. The following examples are offered by way of illustration, not by way of limitation.

Example I

Most Warm Autoantibodies Are Phospholipid Directed.

This example describes experiments that demonstrate that addition of phospholipids to warm autoantibody-containing serum significantly neutralizes the warm autoantibodies and reduces or eliminates warm autoantibody binding to RBCs in preparation for standard antiglobulin assays.

Neutralization studies using anionic and cationic phospholipids were conducted using 0.1 M suspensions of five phospholipids. Two anionic phospholipids (cardiolipin, CL; and phosphatidylglycerol, PG) and three cationic phospholipids (phosphatidylethanolamine, PE; phosphatidylcholine, PC; phosphatidylserine, PS) were prepared in normal saline as saturated suspensions. Two drops of each suspension was added to 0.5 milliliter (ml) of patient sera known by Coombs and antiglobulin testing to contain warm autoantibody. The sera and phospholipid suspensions were incubated at 37° C. for 30 minutes. An equal amount of saline was added to a second aliquot as a control for any dilutional effect.

A Coombs test (i.e, a direct antiglobulin test) was used to measure the effect of addition of the phospholipids on the ability of warm autoantibodies in the serum samples to bind RBCs. The Coombs test detects the presence of human IgG bound to red blood cells and was carried out. When a Coombs reagent (anti IgG) is added to washed and sensitized cells that contain IgG on their surface, an agglutination reaction is expected. The strength of this reaction is generally graded from negative (0) to complete agglutination (4+). The strength of the reaction is a reflection of the titer and strength of the antibody. A negative or reduced reaction with the cells in the presence of the phospholipid reagent indicates that the antibody has been completely or partially neutralized by the phospholipid reagent.

The treated sera were tested against a reagent red cell suspension that had previously been determined to be positive by Coombs reaction against the patient's neat (i.e., unaltered) serum and determined to have warm autoantibody by ARC or DTM testing. The loss of agglutinating activity following addition of phospholipids to the patient's serum is indicative of neutralization of warm autoantibodies in the serum.

A total of 36 serum samples were tested. The results of these tests are provided in Table II. In two samples there was no reduction in reactivity following incubation with any phospholipid reagent. In thirty-four samples (94.1%) there was complete or partial reduction in autoantibody reactivity to at least one phospholipid reagent.

Results in Table II are graded on a standard 0–4+ scale in which 0=no agglutination or hemolysis; W+=tiny agglutinates/turbid background; 1+=small agglutinates/turbid background; 2+=medium agglutinates/clear background; 3+=several large agglutinates/clear background; and 4+=one solid agglutinate.

TABLE II

Phospholipid neutralization patterns with anionic and cationic phospholipids in patients with warm autoreactivity in serum.

| sample # | Neat | CL | PG | PE | PC | PS |
|---|---|---|---|---|---|---|
| 1. | 1+ | 0 | 0 | 1+ | 1+ | nt |
| 2. | w+ | 0 | 0 | w+ | w+ | nt |
| 3. | 1+ | 0 | 0 | 1+ | 1+ | nt |
| 4. | w+ | 0 | 0 | w+ | w+ | nt |
| 5. | w+ | 0 | 0 | w+ | w+ | nt |
| 6. | 1+ | 0 | 0 | 1+ | 1+ | nt |
| 7. | 1+ | 0 | 0 | 1+ | 1+ | nt |
| 8. | 2+ | 0 | 0 | 0 | 0 | nt |
| 9. | 3+ | 0 | 0 | 0 | 0 | nt |
| 10. | 2+ | 0 | 0 | 0 | 0 | nt |
| 11. | 3+ | 0 | 0 | 0 | 0 | nt |
| 12. | 2+ | 0 | 0 | 0 | 0 | nt |
| 13. | 3+ | 0 | 0 | 0 | 0 | nt |
| 14. | 3+ | 1+ | 1+ | 1+ | 1+ | nt |
| 15. | 2+ | 0 | 0 | 0 | 0 | nt |
| 16. | 3+ | 3+ | 3+ | w+ | w+ | nt |
| 17. | 1+ | 1+ | 1+ | 0 | 0 | nt |
| 18. | 1+ | 1+ | 1+ | 0 | 0 | nt |
| 19. | 3+ | w+ | w+ | 3+ | 3+ | nt |
| 20. | w+ | 0 | 0 | 0 | 0 | nt |
| 21. | w+ | 0 | 0 | w+ | w+ | nt |
| 22. | w+ | 0 | 0 | w+ | w+ | nt |
| 23. | 1+ | 0 | 0 | 1+ | 1+ | nt |
| 24. | w+ | 0 | 0 | w+ | w+ | nt |
| 25. | w+ | 0 | 0 | w+ | w+ | nt |
| 26. | 2+ | 0 | 0 | 0 | 0 | nt |
| 27. | 2+ | 0 | 0 | 0 | 0 | nt |
| 28. | 3+ | 1+ | 1+ | 1+ | 1+ | w+ |
| 29. | 3+ | 3+ | 3+ | 3+ | w+ | 3+ |
| 30. | 4+ | 4+ | 4+ | 4+ | 1+ | 4+ |
| 31. | 1+ | 1+ | 1+ | 1+ | 0 | 1+ |
| 32. | 1+ | 0 | 0 | 1+ | 1+ | 1+ |
| 33. | W+ | 0 | 0 | W+ | W+ | W+ |
| 34. | W+ | 0 | 0 | W+ | W+ | W+ |
| 35. | 3+ | 3+ | 3+ | 3+ | 3+ | 3+ |
| 36. | 3+ | 3+ | 3+ | 3+ | 3+ | 3+ |

Example II

Preparation and use of a 3-PGA/phosphatidylcholine column.

A. Preparation of column.

Spin-columns containing the warm autoantibody-binding ligands 3-phosphoglyceric acid (3-PGA) and phosphatidylcholine were prepared according to the following protocol.

i) Binding ligands to activated agarose.

In separate test tubes, 5 ml of activated agarose [Sigma Chemical Co. Cat # A-0802] was added to 10 ml of 0.001 M 3-PGA [barium salt, Sigma, Cat. P-8627] in phosphate buffered saline (PBS) and 5 ml of Agarose was added to 10 ml of 0.001 M phosphatidylcholine in PBS. Each tube was rocked at room temp (20–25° C.) for 30 min, followed by centrifugation for 5 minutes at 3500 rpm in a Sorval RT 6000D. The supernatant was decanted and the agarose washed by resuspending in PBS and repeating the centrifugation and decanting steps twice. Each batch of washed agarose was resuspended in 10 mls PBS.

ii) Pouring spin columns.

Two mls each of the 3-PGA and PC were added to a spin column (a Sigma Microcentrifuge filter, Cat. # UFC4TMK25, with the filter removed and replaced with filter paper was used). The column was centrifuged to dryness (10 minutes at 3000 rpm in a Sorval RT600D tabletop centrifuge) to remove the PBS and the resin blocked by resuspending in 4 ml of 1% human serum albumin (HSA) or 1% BSA in PBS followed by incubation at room temperature for 1 hour. The column was washed 2× with PBS and stored at 6° C.

B. Use of column

Columns prepared as above were used as follows:
1. The spin column was centrifuged to dryness.
2. Approximately 2 ml of serum were loaded onto the column and mixed gently with the activated matrix.
3. The column containing serum was incubated at 37° C. for at least 1 hour.
4. The column was centrifuged to harvest the warm autoantibody-depleted serum.
5. The column eluate was used for antiglobulin testing.

Example III

Removal of warm autoantibodies from serum using 3-PGA/Phosphatidylcholine spin columns Serum samples were obtained from the Red Cross [Red Cross National Reference Library, Crabbs Branch Way, Rockville, Md.] or the Department of Transfusion Medicine, Clinical Center, National Institutes of Health, and the underlying alloantibody reactivity (if any) was determined after removal of warm autoantibodies by conventional methods (i.e., autoadsorption or differential adsorption). The samples were therefore tested against reagent red cells that were antigen negative for the identified alloantibody(s). This gave an accurate reflection of the strength of the warm autoreactivity, and allowed measurement of the effectiveness of a column containing 3-PGA and phosphatidylcholine. Alloantibody reactivity in most samples was not reconfirmed in a panel test following adsorption because the quantity of serum available was not sufficient.

Figure 2:
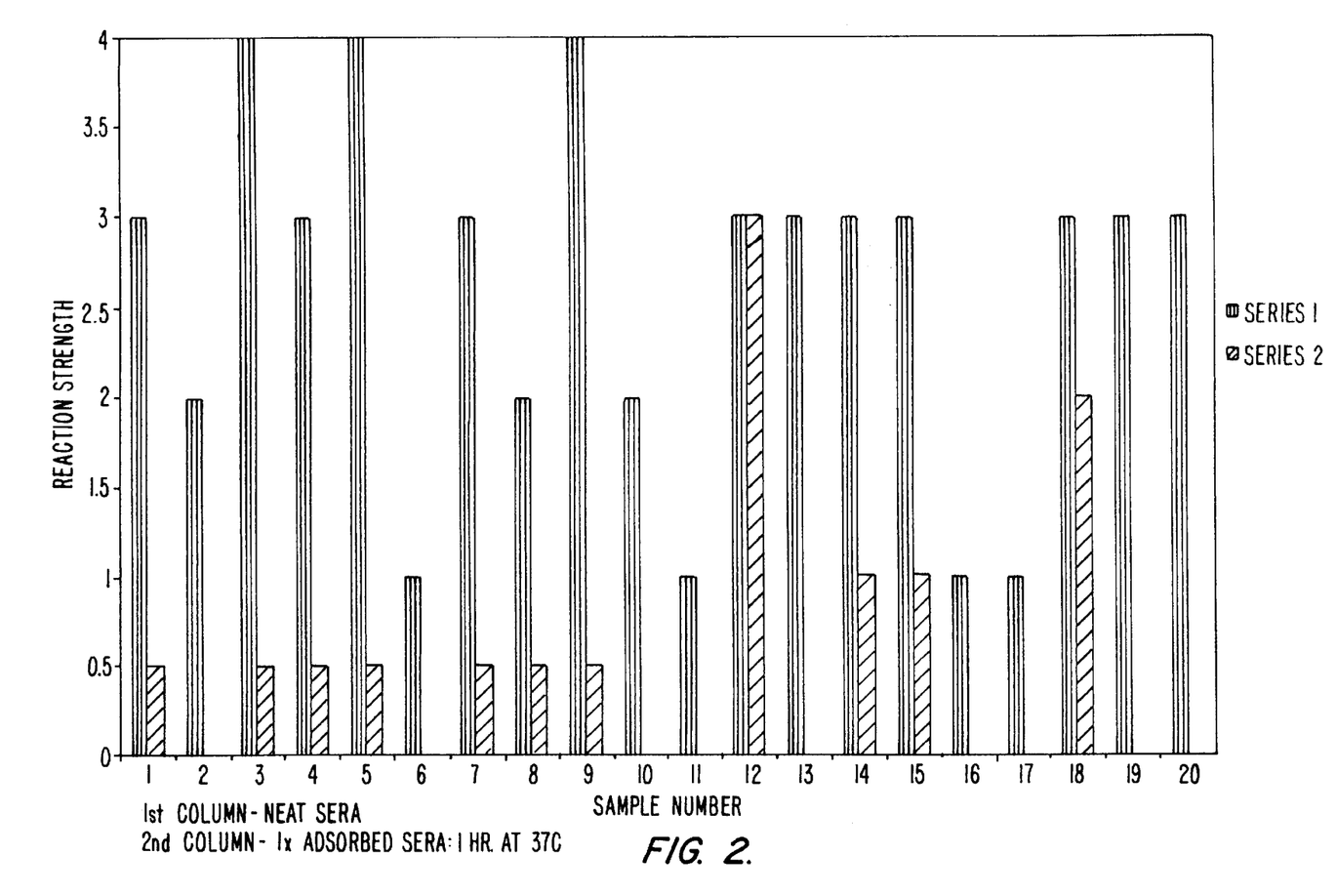
FIG. 2 shows adsorption of warm autoantibodies from serum using 3-phosphoglyceric acid (3-PGA) and phosphotidylcholine conjugated to activated agarose beads. In this figure and in FIG. 3, the absence of a second data bar for a sample indicates that the reaction strength for the adsorbed serum was 0.

Twenty serum samples were adsorbed with a small (0.5 ml bed volume) two-piece spin column that contained 3-phosphoglyceric acid and phosphatidylcholine as ligands on an activated agarose matrix. Of these samples, 9 had RBC reactivity removed completely as assessed by indirect Coombs tests, 18 had reactivity reduced by more than 50%, and 10 had a partial reduction. These results are shown in FIG. 2. One sample (#12) had no reduction in reactivity observed. The consistent strength in the reduction of the reactivity seemed to indicate that the column was effective, but was unable to completely remove autoreactivity from most of the strongest reacting (3+ and 4+) samples, suggesting that somewhat larger columns or multiple incubations would be useful.

Figure 3:
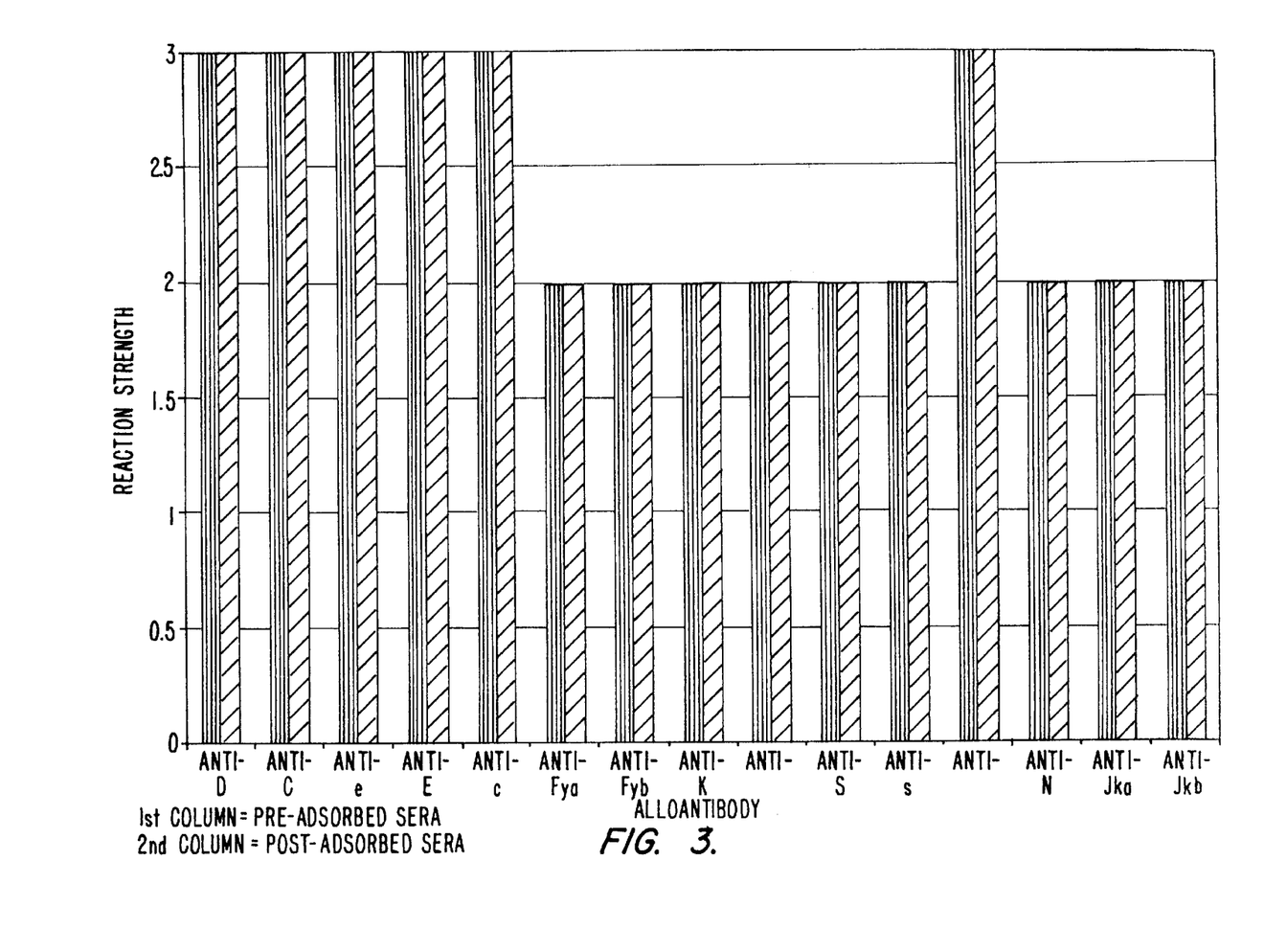
FIG. 3 shows that a 3-PGA/phosphotidylcholine column does not adsorb alloantibodies.

Alloantibody controls using commercial antiserum was also tested to ensure that no reduction of any clinically significant alloantibody occurred using these ligands. Sources for commercial alloantibodies included Ortho (bioclone), Immucor, and Gamma Biologicals. The results of this experiment are shown in FIG. 3. Use of the column with commercial antisera containing known alloantibodies resulted in no reduction of alloantibody reactivity.

Example IV

Figure 4:
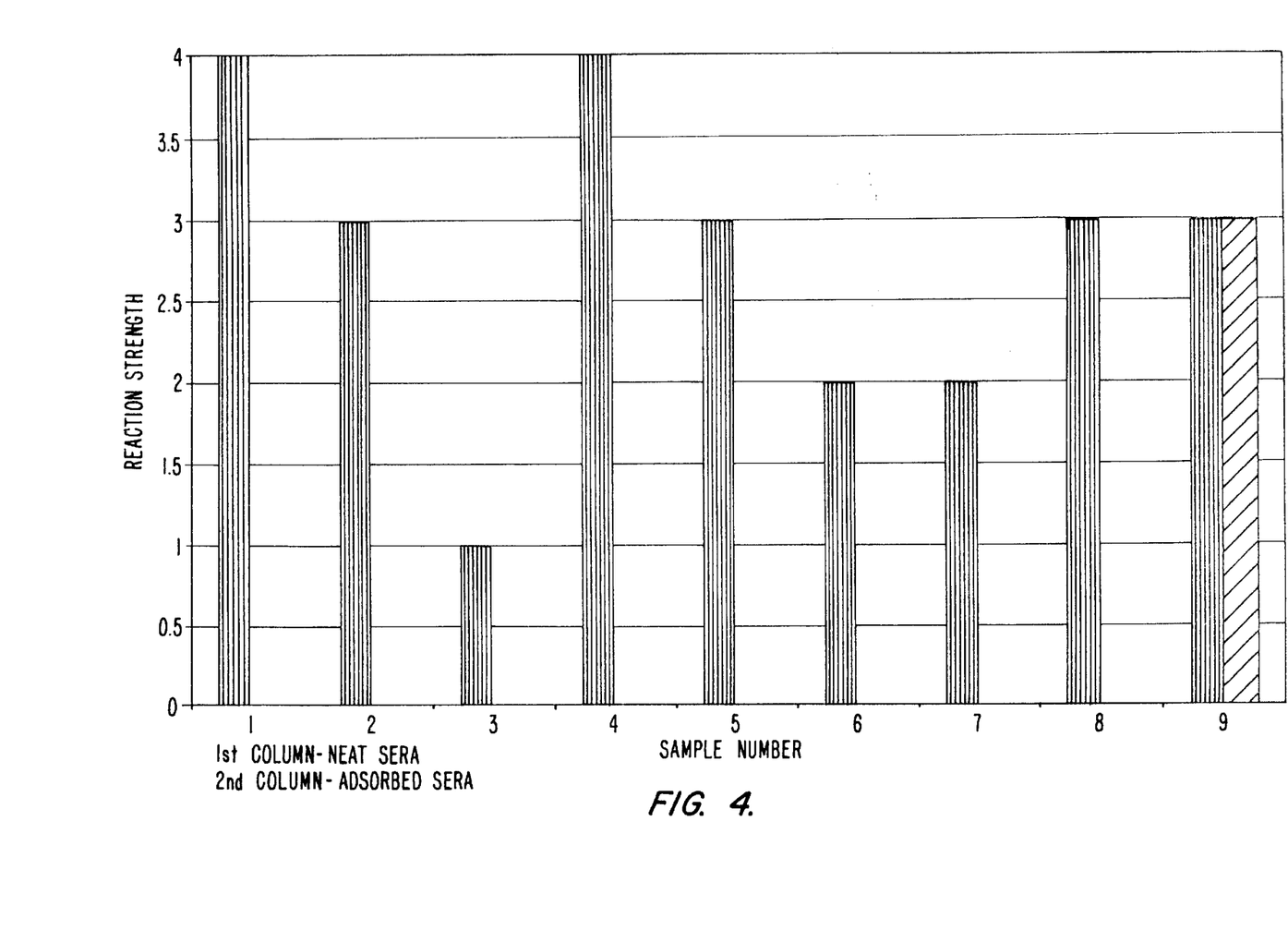
FIG. 4 shows adsorption of warm autoantibodies from serum using 3-PGA and phosphocholine conjugated to activated agarose.
Figure 5:
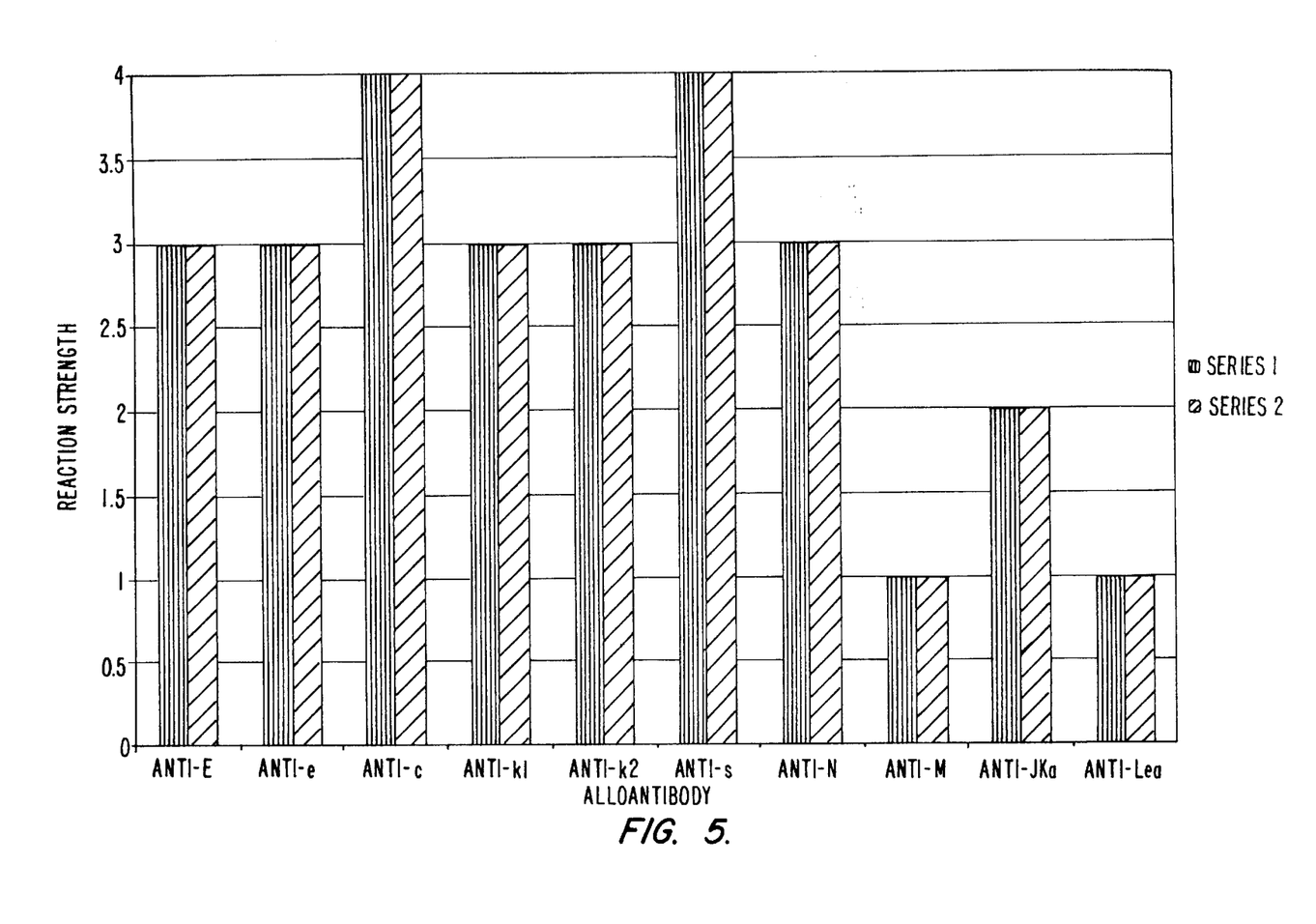
FIG. 5 shows that a 3-PGA/phosphocholine column does not adsorb alloantibodies.

Removal of warm autoantibodies from serum using 3-PGA/phosphocholine spin columns A larger column than those used in Example III was designed in order to present more antigen and improve adsorption of warm autoantibody from the strongest reacting (3+ and 4+) samples. In addition, phosphocholine chloride was substituted for phosphatidylcholine in the column. Phosphocholine differs from phosphatidylcholine in that it lacks fatty acid chains. This larger column was tested against an additional 9 serum samples with previously identified warm autoreactivity. Of these samples, 8 had a complete reduction in Coombs reactivity (FIG. 4). In one sample no reduction was observed. Use of the column with commercial antisera containing known alloantibodies resulted in no reduction of alloantibody reactivity (FIG. 5).

Example V

Assessment of the warm autoantibody- and alloantibody-binding characteristics of a ligand.

The binding characteristics of a particular compound are determined empirically. A phospholipid, phosphoric acid ester typically associated with phospholipids, or a naturally occurring or synthetic analogue of the above-recited molecules, as described supra, is selected and bound to an activated matrix such as adipic acid dihydrazide-agarose according to procedures recommended by the matrix supplier. Following binding the matrix is blocked by incubation at room temperature for 1 hour in 1% HSA or BSA in PBS (or other blocking agents reactive with the functional binding group of the activated matrix), followed by washing 2× with PBS. The blocking step prevents indiscriminate removal of serum proteins by any unbound sites on the activated matrix. Several spin columns are then prepared by loading the matrix into the upper chamber of a 2-piece spin column.

Using the spin columns so prepared, the compound is tested against a number of warm autoantibody-containing serum samples as described in Example III, and the reduction in reactivity is determined. Screening between 20 and 50 serum samples, preferably about 30 serum samples, will provide an estimate as to the percentage of serum samples containing warm autoantibodies bound by the compound being tested.

The new compound is also tested against clinically significant alloantibodies in order to test whether any reduction in reactivity that would indicate adsorption would occur. Any significant reduction in clinically significant alloreactivity will usually indicate that the compound is unacceptable for removing warm autoantibodies.

Example VI

Direct neutralization of warm autoantibody may be achieved by adding a warm autoantibody-binding ligand directly to the sera. This is done by preparing a saturated solution of the ligand (about 0.05–0.5 M) in a buffered medium (e.g., PBS, normal saline). Two drops (about 100 µl) of the ligand is added in a centrifuge tube to 0.5 ml of the serum sample to be tested. As a control to ensure that any reduction in reactivity seen is not due to a dilutional effect, a second aliquot of sera of equal volume is also tested with 2 drops of the medium only.

The samples are incubated at 37° C. for 15 to 90 minutes and then centrifuged for 3 min at 3000 rpm (in order to remove any excess ligand that has not been dissolved into the sera). The serum sample is transferred to a clean tube and tested using standard antiglobulin testing.

What is claimed is:

1. A method for antiglobulin testing of serum from a patient comprising the steps:

a) obtaining a test sample of the patient's serum;

b) contacting the test sample with at least one ligand that binds warm autoantibodies but does not bind alloantibodies, wherein the ligand is selected from the group consisting of phospholipids, polar head groups of phosphoglycerides, and analogues of said phospholipids and polar head groups, wherein the ligand is synthetically conjugated to a support matrix, and wherein the contacting results in warm autoantibodies being specifically bound to the ligand to produce bound warm autoantibodies, and wherein other serum components are not specifically bound;

c) separating the other serum components from the bound warm autoantibodies; and d) testing the other serum components for antiglobulin with an antiglobulin test.

2. The method of claim 1 wherein the test sample is contacted with at least two different ligands that bind warm autoantibodies but do not bind alloantibodies.

3. The method of claim 1 wherein the ligand is an analogue of a phospholipid or polar head group and is selected from the group consisting of: O-phospho-DL-serine, O-phospho-L-tyrosine, phosphoenolpyruvic acid, 2(phosphonomethyl)acrylic acid, Nω-phospho-L-arginine, phosphocolamine,6-phosphogluconic acid Tris (cyclohexylamine)salt, 6-phosphogluconic acid, D-2-phosphoglyceric acid, O-phospho-D-serine, O-phospho-L-serine, O-phospho-L-threonine, O-phospho-D-threonine, 3-phosphoglyceric acid, phosphocholine, O-phosphoethanolamine and 3'-O-lysylphosphoglycerol.

4. The method of claim 3 wherein the ligand is selected from the group consisting of: O-phospho-D-serine, O-phospho-L-serine, O-phospho-L-threonine, O-phospho-D-threonine, 3-phosphoglyceric acid and phosphocholine.

5. The method of claim 2 wherein the test sample is contacted with the ligands 3-phosphoglyceric acid and phosphocholine.

6. The method of claim 5 wherein the phosphocholine is phosphocholine chloride.

7. The method of claim 2 wherein the test sample is contacted with the ligands 3-phosphoglyceric acid and phosphatidylcholine.

8. The method of claim 1 wherein the ligand is a phospholipid.

9. The method of claim 8 wherein said phospholipid is an anionic phospholipid.

10. The method of claim 8 wherein the phospholipid is selected from the group consisting of: phosphatidic acid, phosphatidylethanolamine, phosphatidylcholine, phosphatidylserine, phosphatidylglycerol, cardiolipin (diphosphatidylglycerol), phosphatidylinositol, and 3'-O-lysylphosphotidylglycerol.

11. The method of claim 10 wherein the phospholipid is phosphatidylchloline.

12. The method of claim 1 wherein bound warm autoantibodies and the other serum components are separated by column chromatography.

13. The method of claim 1 wherein the support matrix is agarose or adipic acid dihydrazide-agarose.

14. The method of claim 1 wherein the antiglobulin test is a compatibility test or a cross-matching test.

15. A kit comprising a spin column comprising a lower chamber and a removably housed upper chamber having a top and a bottom, said kit further comprising 3-phosphoglyceric acid and phosphocholine, each conjugated to a support matrix, wherein the upper chamber can be reversibly sealed at both the top and the bottom.

16. The kit of claim 15 wherein the 3-phosphoglyceric acid and phosphocholine, each conjugated to a support matrix are situated within the upper chamber.

17. The kit of claim 16 further comprising a preservative in the upper chamber.

18. The kit of claim 16 further comprising instructions for preparing serum for antiglobulin screening.

19. A kit comprising a spin column comprising a lower chamber and a removably housed upper chamber having a top and a bottom, wherein the upper chamber can be reversibly sealed at both the top and the bottom, said kit further comprising 3-phosphoglyceric acid and phosphatidylcholine, each conjugated to a support matrix.

20. A kit comprising a spin column comprising a lower chamber and a removably housed upper chamber having a top and a bottom, wherein the upper chamber can be reversibly sealed at both the top and the bottom, said kit further comprising O-phospho-D-serine and O-phospho-D-threonine, each conjugated to a support matrix.

* * * * *